(12) United States Patent
Bobrow

(10) Patent No.: US 7,291,474 B2
(45) Date of Patent: Nov. 6, 2007

(54) HYDROLYTIC SUBSTRATES FOR AN ANALYTE-DEPENDENT ENZYME ACTIVATION SYSTEM

(75) Inventor: Mark N. Bobrow, Lexington, MA (US)

(73) Assignee: PerkinElmer LAS, Inc., Boston, MA (US)

( * ) Notice: Subject to any disclaimer, the term of this patent is extended or adjusted under 35 U.S.C. 154(b) by 0 days.

(21) Appl. No.: 10/560,577

(22) PCT Filed: Jun. 10, 2004

(86) PCT No.: PCT/US2004/018524

§ 371 (c)(1),
(2), (4) Date: Jun. 23, 2006

(87) PCT Pub. No.: WO2004/111259

PCT Pub. Date: Dec. 23, 2004

(65) Prior Publication Data

US 2007/0020681 A1  Jan. 25, 2007

Related U.S. Application Data

(60) Provisional application No. 60/320,262, filed on Jun. 12, 2003.

(51) Int. Cl.
| | |
|---|---|
| G01N 33/53 | (2006.01) |
| G01N 33/573 | (2006.01) |
| G01N 33/533 | (2006.01) |
| G01N 21/76 | (2006.01) |
| C12Q 1/34 | (2006.01) |
| C07C 22/08 | (2006.01) |
| C07K 1/10 | (2006.01) |
| C12N 3/38 | (2006.01) |

(52) U.S. Cl. ........................ 435/7.1; 435/7.4; 435/7.72; 435/18; 435/968; 435/207; 436/164; 436/546; 530/402; 570/127

(58) Field of Classification Search ................ 435/7.4, 435/7.72, 21, 20, 7.1, 968, 207, 18; 436/546, 436/164; 530/391.5, 402; 570/127
See application file for complete search history.

(56) References Cited

U.S. PATENT DOCUMENTS 5,583,001 A * 12/1996 Bobrow et al. .............. 435/7.5

| | | |
|---|---|---|
| 5,863,748 A | 1/1999 | Bobrow |
| 6,355,443 B1 | 3/2002 | Bobrow et al. |
| 6,399,299 B1 | 6/2002 | Bobrow et al. |
| 2004/0235081 A1* | 11/2004 | Burton ........................ 435/23 |

OTHER PUBLICATIONS

Lo, Lee-Chiang, et al, Design and Synthesis of Class-Selective Activity Probes for Protein Tyrosine Phosphatases, Journal of Proteome Research 2002, 1, 35-40, Nov. 1, 2002.
Tsai, Charng-Sheng, et al., Design and Synthesis of Activity Probes for Glycosidases, 2002 American Chemical Society, vol. 4, No. 21, pp. 3607-3610, Nov. 21, 2002.
Zhu, Qing, et al., Activity-based fluorescent probes that target phosphatases, 2003 Elsevier Science Ltd., Tetrahedron Letters 44 (2003) 2669-2672.
Chen, Y.J. Grace, et al., Developing a Strategy for Activity-Based Detection of Enzymes in a Protein Microarry, ChemBioChem 2003, No. 4, pp. 336-339.

* cited by examiner

Primary Examiner—Long V. Le
Assistant Examiner—Shafiqul Haq
(74) Attorney, Agent, or Firm—Gifford Krass Sprinkle Anderson & Citkowski

(57) ABSTRACT

Disclosed are compounds of the general formulas:

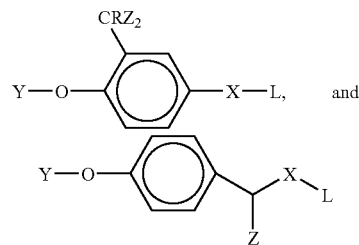

wherein Y is a moiety capable of being cleaved by a hydrolytic enzyme; L is a detectable label; X is a linking group; Z is a halogen; and R is hydrogen, an alkyl, or a halogen. Compounds of this general formula can be used as substrates in an analyte-dependent enzyme activation system, such as that employed in connection with catalyzed reporter depositions. Also disclosed are assays using the compounds, and kits for carrying out the assays.

19 Claims, No Drawings

HYDROLYTIC SUBSTRATES FOR AN ANALYTE-DEPENDENT ENZYME ACTIVATION SYSTEM

RELATED APPLICATION

This application claims priority of U.S. Provisional Patent Application Ser. No. 60/320,262 filed Jun. 12, 2003 entitled "2-Difluoromethylphenyl-Containing Substrates for an Analyte Dependent Enzyme Activation System."

FIELD OF THE INVENTION

This invention relates generally to chemical compounds which are substrates for hydrolytic enzymes and to analyte-dependent enzyme activation system assays which utilize the substrate compounds.

BACKGROUND OF THE INVENTION

Catalyzed reporter deposition (CARD) is a novel method of signal amplification which constitutes the subject matter of U.S. Pat. Nos. 5,731,158; 5,583,001 and 5,196,306. These patents, and all other patents referred to herein, are incorporated by reference. Assays employing this technique are also described in Bobrow et al., Journal of Immunological Methods, 125:279-285 (1989) and in Bobrow et al., Journal of Immunological Methods, 137-103-112 (1991).

The CARD method utilizes an analyte-dependent enzyme activation system ("ADEAS") to catalyze the deposition of reporter or hapten groups, collectively referred to as "labels," onto a receptor, the receptor being part of or added to a surface in contact with the components of the assay. These enzymatically deposited labels are detected directly or indirectly, resulting in signal amplification and improved detection limits. In the previously disclosed references, a peroxidase was the preferred enzyme. While peroxidase enzymes give reliable assay results, the kinetics of the peroxidase reaction are, in some instances, overly rapid. Such rapid kinetics can decrease the dynamic range of the assay, making it difficult to collect quantitative data over broad ranges. Hydrolytic enzymes, also referred to as hydrolases, generally have slower kinetics, and it is desirable to incorporate them in these assays.

In the CARD method, an enzyme reacts with a conjugate consisting of a labeled compound incorporated into an enzyme substrate. When the enzyme and the substrate react, a reactive intermediate, also termed an "activated conjugate," is formed which binds covalently wherever receptor for the reactive intermediate is immobilized. Examples of such compounds which have been described for use with peroxidase enzymes include substituted phenols such as biotinyl-tyramide, fluorescein tyramide and p-hydroxycinnamoyl-containing substrates disclosed in U.S. Pat. No. 5,863,748, as well as the 4-(4-hydroxystyryl)pyridine substrates disclosed in U.S. Pat. No. 6,355,443.

In other analyses of the prior art, enzyme substrates have been used to generate products which become colored, fluorescent or chemiluminescent. These products either remain soluble or become insoluble and precipitate on a surface. The CARD method differs in that the reactive intermediates become covalently bound to the receptor, which may be part of, or separately, immobilized on a surface.

2-difluoromethylphenyl and p-hydroxymandelic acid compounds are well known for use as, for example, activity-based probes, Zhu et al., (2003) Tetrahedron Letters, 44, 2669-2672, Lo et al., (2002) J. Proteome Res., 1, 35-40; screening of antibody libraries, Cesaro-Tadic et al., (2003) Nature Biotechnology, 21, 679-685, Janda et al., (1997) Science 275, 945-948; and suicide substrates, Halazy et al., (1990) Bioorganic Chemistry 18, 330-344, Betley et al., (2002) Angew. Chem. Int. Ed. 41, 775-777. However, none of these references teaches the use of these compounds as substrates for detection and amplification in analyte-dependent assays such as immunoassays, nucleic acid hybridization assays, microarray assays, immunohistochemical applications, in-situ hybridization applications and the like.

SUMMARY OF THE INVENTION

Disclosed herein are compounds which may be used as substrates in an assay such as a catalyzed reporter deposition utilizing an analyte-dependent enzyme activation system. The compounds are of the general formulas:

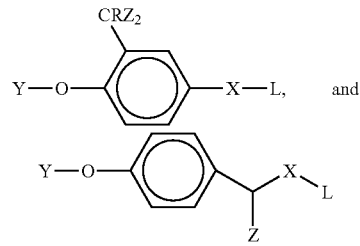

wherein Y is a moiety capable of being cleaved by a hydrolytic enzyme; L is a detectable label; X is a linking group; Z is a halogen, and R is hydrogen, an alkyl, or a halogen. In specific embodiments, R is hydrogen and the Z groups are fluorine.

In certain embodiments, Y is a phosphate, a phosphate ester, a glycoside, or an alkyl ester. L may be a fluorescent label or it may be a member of a binding pair, and in that regard may be biotin or dinitrophenyl.

Also disclosed herein is an assay utilizing these materials, as well as a kit for carrying out such assays.

DETAILED DESCRIPTION OF THE INVENTION

The present invention relates to a method for detecting or quantitating an analyte, employing an analyte-dependent enzyme activation system which reacts with a substrate portion of a conjugate which comprises a detectably labeled substrate for said enzyme, so as to form an activated conjugate, which activated conjugate covalently binds to a site having a receptor for said activated conjugate, said receptor not being reactive with the analyte-dependent enzyme activation system, wherein the detectably labeled portion of the bound conjugate either directly or indirectly generates a signal which is detected or quantitated, wherein in one group of embodiments, said conjugate is a compound having the structure:

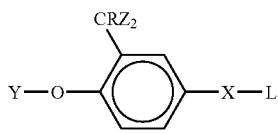

wherein Y is a moiety capable of being cleaved by a hydrolytic enzyme; L is a detectable label; X is a linking group; Z is a halogen; and R is hydrogen, an alkyl or a halogen.

In one specific embodiment, the substrate compound is of the general formula:

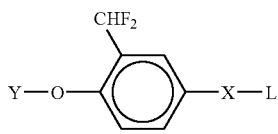

wherein Y, X and L are as above. In one group of materials in accord with this embodiment, Y is a phosphorous-free material such as glycoside esters, alkyl esters and the like. In other instances, the Z group may be chlorine or other halogens.

In another embodiment, the present invention further relates to a method for detecting or quantitating an analyte, employing an analyte-dependent enzyme activation system which reacts with a substrate portion of a conjugate which comprises a detectably labeled substrate for said enzyme, so as to form an activated conjugate, which activated conjugate covalently binds to a site having a receptor for said activated conjugate, said receptor not being reactive with the analyte-dependent enzyme activation system, wherein the detectably labeled portion of the bound conjugate either directly or indirectly generates a signal which is detected or quantitated, wherein said conjugate is a compound having the structure:

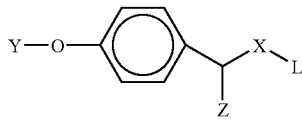

wherein Y is a moiety capable of being cleaved by a hydrolytic enzyme, L is a detectable label, X is a linking group and Z is a halogen. One group of materials in accord with this embodiment are fluorinated mandelic acid derivatives. In other instances, chlorine or other halogens may comprise the Z group.

In the various embodiments, moieties capable of being cleaved by hydrolytic enzymes include phosphate esters, glycoside esters such as galactose and glucose, and alkyl esters cleavable by non-specific esterases.

The linker group X can be virtually any linker group capable of linking the detectable label to the hydrolytic enzyme cleavable moiety, and the invention is not limited to the use of any specific linkers. In some instances, the linker may be a portion of the label L. Any linear or branched alkyl ($C_1$ to $C_{10}$ for example), heteroatom substituted alkyl, or aryl group can serve as a linker, the only requirement being that it links the phenyl moiety with the label.

The term "analyte-dependent enzyme activation system" (ADEAS) refers to an enzyme system wherein (i) at least one enzyme is coupled, in any manner known to those skilled in the art, to a member of a specific binding pair, or (ii) the enzyme need not be coupled to a member of a specific binding pair when it is the analyte. The enzyme, either by itself or in connection with a second enzyme, reacts with the substrate conjugate of the present invention and catalyzes the formation of a reactive intermediate which then is deposited wherever there is a receptor for the reactive intermediate.

The term "surface" as used herein means any solid support or phase known to those skilled in the art including cells, tissues, membranes, slides, and beads.

The term "amplification" as used herein means amplification of reporter signal.

The term "reactive intermediate" means the substrate portion of the conjugate has been primed by the enzyme to bind to the receptor.

The term "receptor" means a site which will bind to the reactive intermediate through the formation of a covalent bond.

The term "detectably labeled" means that the conjugate, in addition to having a substrate moiety, also has a reporter or an unlabeled first member of a specific binding pair moiety. In the case in which there is an unlabeled member of a specific binding pair, after the reactive intermediate is covalently bound to the receptor, the substrate-specific binding pair complex is reacted with the second member of the binding pair which is coupled to a reporter so as to produce a detectable signal.

Members of specific binding pairs suitable for use in practicing the invention can be of the immune or non-immune type. Immune specific binding pairs are exemplified by antigen/antibody systems or hapten/anti-hapten systems such as dinitrophenyl (DNP)-anti-DNP. The antibody member, whether polyclonal, monoclonal or an immunoreactive fragment thereof, of the binding pair can be produced by customary methods familiar to those skilled in the art. The terms "immunoreactive antibody fragment" or "immunoreactive fragment" mean fragments which contain the binding region of the antibody. Such fragments may be Fab type fragments which are defined as fragments devoid of the Fc portion, e.g., Fab, Fab' and F(ab')2 fragments, or may be so-called "half molecule" fragments obtained by reductive cleavage of the disulfide bonds connecting the heavy chain components of the intact antibody. If the antigen member of the specific binding pair is not immunogenic, e.g., a hapten, it can be covalently coupled to a carrier protein to render it immunogenic.

Non-immune binding pairs include systems wherein the two components share a natural affinity for each other but are not antibodies. Exemplary non-immune binding pairs are biotin-avidin or biotin-streptavidin, folic acid-folate binding protein, complementary probe nucleic acids, etc. Also included are non-immune binding pairs which form a covalent bond with each other. Exemplary covalent binding pairs include sulfhydryl reactive groups such as maleimides and haloacetyl derivatives and amine reactive groups such as isothiocyanates, succinimidyl esters, sulfonyl halides, and coupler dyes such as 3-methyl-2-benzothiazolinone hydrazone (MBTH) and 3-(dimethyl-amino)benzoic acid (DMAB), etc.

The term "deposition" means directed binding of a reactive intermediate to the receptor which results from the formation of a covalent bond.

In the operation of the assay, the enzyme catalyzes the deposition of a reporter by converting the substrate component of the conjugate to a reactive intermediate which is capable of covalently binding to a receptor. Enzymes suitable for use with the present invention include hydrolases. More particularly, phosphatases, glycosidases and esterases can be employed. Some specific enzymes which are suitable for the novel substrates of the invention include alkaline phosphatases and beta-galactosidase.

A wide variety of detectable labels are available for linking to the substrate moiety, and the present invention is not limited to any specific label. The detectable label can be a reporter such as a radioactive isotope such as $^{125}I$, enzymes, fluorescent reagents or groups such as fluorescein, tetramethylrhodamine, cyanine dyes, Alexa dyes or BODIPY dyes, chemiluminescent reagents or groups, or electrochemical materials. The detectable label can also be a member of a specific binding pair as described above. Other labels will be readily apparent to one of skill in the art.

Exemplary substrate moieties useful for the present invention include 2-difluoromethylphenyl and p-hydroxymandelic acid moieties.

The present invention provides labeling and enhanced signal generation in a variety of applications, including but not limited to ELISA, blotting assays, immunohistochemical analysis, in-situ hybridization, nucleic acid microarrays, protein or peptide microarrays, cell and tissue arrays, and cell and tissue lysate arrays.

The foregoing discussion and description sets forth some specific embodiments of materials and methods which may be used in the practice of the invention. Other materials and methods will be apparent to one of skill in the art, and are also within the scope of the invention. The foregoing is illustrative of, but not limiting on, the present invention. It is the following claims, including all equivalents, which define the scope of the invention.

The invention claimed is:

1. In an assay for detecting or quantitating an analyte, wherein in the operation of said assay, said analyte reacts to form a specific binding pair, which is localized on a solid phase support, said assay employing an analyte-dependent enzyme activation system in which the localization of the specific binding pair on the solid phase support localizes an enzyme on said solid phase support, and wherein said localized enzyme reacts with a substrate portion of a conjugate, said conjugate comprising a detectably labeled substrate for said enzyme, so as to form an activated conjugate, which activated conjugate covalently binds to a receptor site for said activated conjugate on said solid phase support proximate where said specific binding pair is localized, said receptor not being reactive with the unactivated conjugate of the analyte-dependent enzyme activation system, wherein the detectably labeled portion of the bound conjugate either directly or indirectly generates a signal which is detected or quantitated, the improvement comprising: using as said conjugate, a compound having a structure selected from the group consisting of:

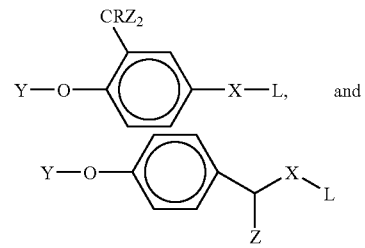

wherein Y is a moiety capable of being cleaved by a hydrolytic enzyme; L is a detectable label; X is a group linking L to the phenyl group; Z is a halogen; and R is selected from hydrogen, halogen and alkyl groups.

2. The assay of claim 1, wherein Z is fluorine.

3. The assay of claim 2, wherein R is hydrogen.

4. The assay of claim 1, wherein Y is selected from the group consisting of: phosphates, phosphate esters, glycosides and alkyl esters.

5. The assay of claim 4, wherein said glycosides are selected from the group consisting of galactose and glucose.

6. The assay of claim 1, wherein L is a first member of a specific binding pair.

7. The assay of claim 1, wherein L is biotin or dinitrophenyl.

8. The assay of claim 1, wherein L is a fluorescent species.

9. The assay of claim 8, wherein L is selected from the group consisting of fluorescein, tetramethylrhodamine, sulforhodamine 101, a cyanine dye, Alexa dye or BODIPY dye.

10. An assay for detecting or quantitating an analyte in a sample which comprises:
   a) immobilizing the analyte on a solid phase to produce a first product comprising a specific binding pair, said specific binding pair having an enzyme associated therewith so that said enzyme is immobilized on said solid phase, said enzyme being reactable with a substrate;
   b) providing a compound which is a substrate for said enzyme, said compound having a structure selected from the group consisting of:

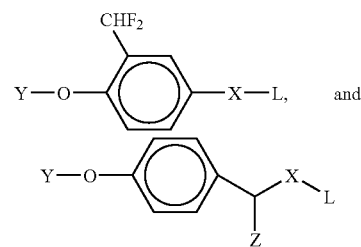

wherein Y is a group capable of being cleaved by said hydrolytic enzyme, L is a reporter and X is a group linking L to the 2-difluoromethylphenyl moiety;
   c) reacting the immobilized enzyme of step a) with said enzyme substrate material so as to form an activated conjugate wherein the activated conjugate binds covalently on the solid phase, wherein deposited detectable labels associated with said conjugate either directly or indirectly generate a signal which is detected or quantitated; and d) detecting or quantitating the analyte in the sample from the signal generated in step c).

11. The assay of claim 10, wherein Y is selected from the group consisting of: a phosphate, a phosphate ester, a glycoside, and an alkyl ester.

12. The assay of claim 10, wherein L is a fluorescent species.

13. The assay of claim 10, wherein L is biotin or dinitrophenyl.

14. A compound having the formula selected from the group consisting of:

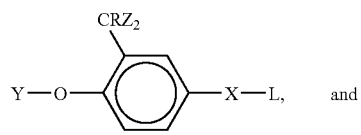

and

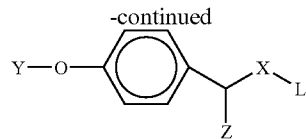

wherein Y is a phosphorus-free group capable of being cleaved by a hydrolytic enzyme, L is a reporter and X is a group linking L to the 2-difluoromethylphenyl moiety.

15. The compound of claim 14, wherein Y is a glycoside.

16. The compound of claim 15, wherein said glycoside is selected from galactose and glucose.

17. The compound of claim 14, wherein Y is an ester.

18. The compound of claim 17, wherein said ester is an alkyl ester.

19. The compound of claim 17, wherein Z is fluorine.

* * * * *